(12) United States Patent
Nicholas

(10) Patent No.: US 11,786,241 B2
(45) Date of Patent: Oct. 17, 2023

(54) SURGICAL STAPLING DEVICE INCLUDING A HYDRAULIC STAPLE FORMATION MECHANISM

(71) Applicant: Covidien LP, Mansfield, MA (US)

(72) Inventor: David A. Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 9 days.

(21) Appl. No.: 17/544,313

(22) Filed: Dec. 7, 2021

(65) Prior Publication Data

US 2022/0257244 A1   Aug. 18, 2022

Related U.S. Application Data

(60) Provisional application No. 63/149,845, filed on Feb. 16, 2021.

(51) Int. Cl.
*A61B 17/068* (2006.01)
*A61B 17/072* (2006.01)
*A61B 17/00* (2006.01)

(52) U.S. Cl.
CPC ........ *A61B 17/0686* (2013.01); *A61B 17/072* (2013.01); *A61B 2017/0046* (2013.01);
(Continued)

(58) Field of Classification Search
CPC .............. A61B 17/0686; A61B 17/072; A61B 17/1155; A61B 2017/00398;
(Continued)

(56) References Cited

U.S. PATENT DOCUMENTS 3,388,847 A   6/1968   Kasulin et al.
3,552,626 A   1/1971   Astafiev et al.
(Continued)

FOREIGN PATENT DOCUMENTS

CA          908529 A    8/1972
CA       2805365 A1    8/2013
(Continued)

OTHER PUBLICATIONS

Engage—definition by Merriam Webster Dictionary, URL https://www.merriam-webster.com/dictionary/engages (Year: 2023).*
(Continued)

*Primary Examiner* — Valentin Neacsu
(74) *Attorney, Agent, or Firm* — Carter, DeLuca & Farrell LLP

(57) ABSTRACT

A shell assembly includes a shell housing defining a cavity, a plurality of staples, a staple cartridge supported on the shell housing, a pusher assembly positioned within the cavity of the shell housing, and a hydraulic piston configured to engage the pusher assembly to impart axial displacement to the pusher assembly and form a fluid tight seal against the shell housing. The staple cartridge defines slots that receive the plurality of staples. The pusher assembly includes a plurality of pushers arranged in an annular configuration to eject the plurality of staples from the staple cartridge. Supply of a fluid into the cavity of the shell housing advances the hydraulic piston, which, in turn, advances the pusher assembly to eject the plurality of staples from the staple cartridge.

20 Claims, 10 Drawing Sheets

(52) U.S. Cl.
CPC .............. *A61B 2017/00486* (2013.01); *A61B 2017/00539* (2013.01); *A61B 2017/07228* (2013.01); *A61B 2017/07257* (2013.01); *A61B 2017/07271* (2013.01); *A61B 2017/07285* (2013.01)

(58) Field of Classification Search
CPC A61B 2017/00539; A61B 2017/00535; A61B 2017/00738
USPC ..................................................... 227/180.1
See application file for complete search history.

(56) References Cited

U.S. PATENT DOCUMENTS

| | | |
|---|---|---|
| 3,606,888 A * | 9/1971 | Wilkinson ......... A61B 17/1152 227/19 |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A * | 3/1993 | Bessler ................ A61B 17/115 600/129 |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A * | 3/1995 | Kuramoto .......... A61B 17/1152 227/19 |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |

(56) References Cited

U.S. PATENT DOCUMENTS

| | | |
|---|---|---|
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |

(56) References Cited

U.S. PATENT DOCUMENTS

| | | |
|---|---|---|
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Tessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |

(56) References Cited

U.S. PATENT DOCUMENTS

| | | |
|---|---|---|
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,553 B2 * | 3/2018 | Cole ................ A61B 17/07292 |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 11,317,945 B2 * | 5/2022 | Williams ............ A61B 17/3468 |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0125826 A1 * | 6/2007 | Shelton, IV ...... A61B 17/07207 |
| | | 227/176.1 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0181322 A1 * | 7/2012 | Whitman ............. A61B 17/068 |
| | | 227/176.1 |
| 2012/0193395 A1 | 8/2012 | Pastorelli et al. |
| 2012/0193398 A1 | 8/2012 | Williams et al. |
| 2012/0232339 A1 | 9/2012 | Csiky |

(56) References Cited

U.S. PATENT DOCUMENTS

| | | |
|---|---|---|
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0284370 A1 | 9/2014 | Sahin |
| 2014/0374465 A1* | 12/2014 | Cole ................. A61B 17/1155 227/177.1 |
| 2015/0083772 A1 | 3/2015 | Miller et al. |
| 2015/0173763 A1 | 6/2015 | Liu |
| 2015/0209045 A1 | 7/2015 | Hodgkinson et al. |
| 2017/0128068 A1 | 5/2017 | Zhang et al. |
| 2020/0330127 A1* | 10/2020 | Williams ........... A61B 17/3468 |
| 2022/0257244 A1* | 8/2022 | Nicholas ........... A61B 17/0686 |

FOREIGN PATENT DOCUMENTS

| | | |
|---|---|---|
| CN | 104039244 A | 9/2014 |
| CN | 104042288 A | 9/2014 |
| CN | 104367360 A | 2/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1671597 A1 | 6/2006 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3023077 A1 | 5/2016 |
| EP | 3243447 A2 | 11/2017 |
| EP | 3412225 A1 | 12/2018 |
| EP | 3549545 A2 | 10/2019 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9835614 A1 | 8/1998 |
| WO | 0154594 A1 | 8/2001 |
| WO | 02080781 A2 | 10/2002 |
| WO | 2004047654 A2 | 6/2004 |
| WO | 2008107918 A1 | 9/2008 |
| WO | 2014008289 A2 | 1/2014 |
| WO | 2019130087 A1 | 7/2019 |

OTHER PUBLICATIONS

Groove—definition by Merriam Webster Dictionary, URL https://www.merriam-webster.com/dictionary/groove (Year: 2023).*

International Search Report dated Jun. 13, 2022 issued in corresponding PCT Appln. No. PCT/US2022/015599.

Extended European Search Report from Appl. No. 14181908.6 dated May 26, 2015.

European Examination Report from Appl. No. 14181908.6 dated May 3, 2016.

* cited by examiner

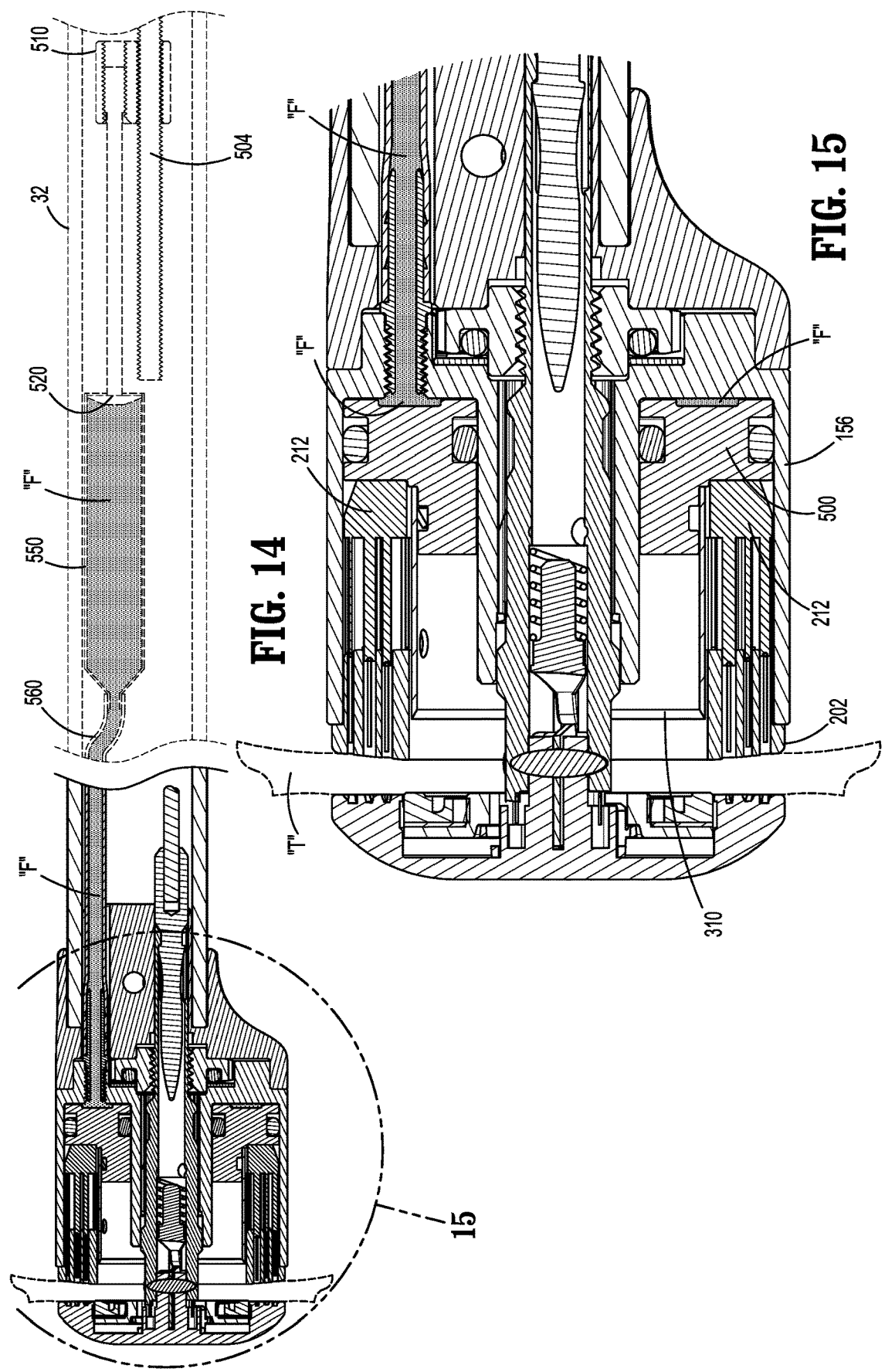

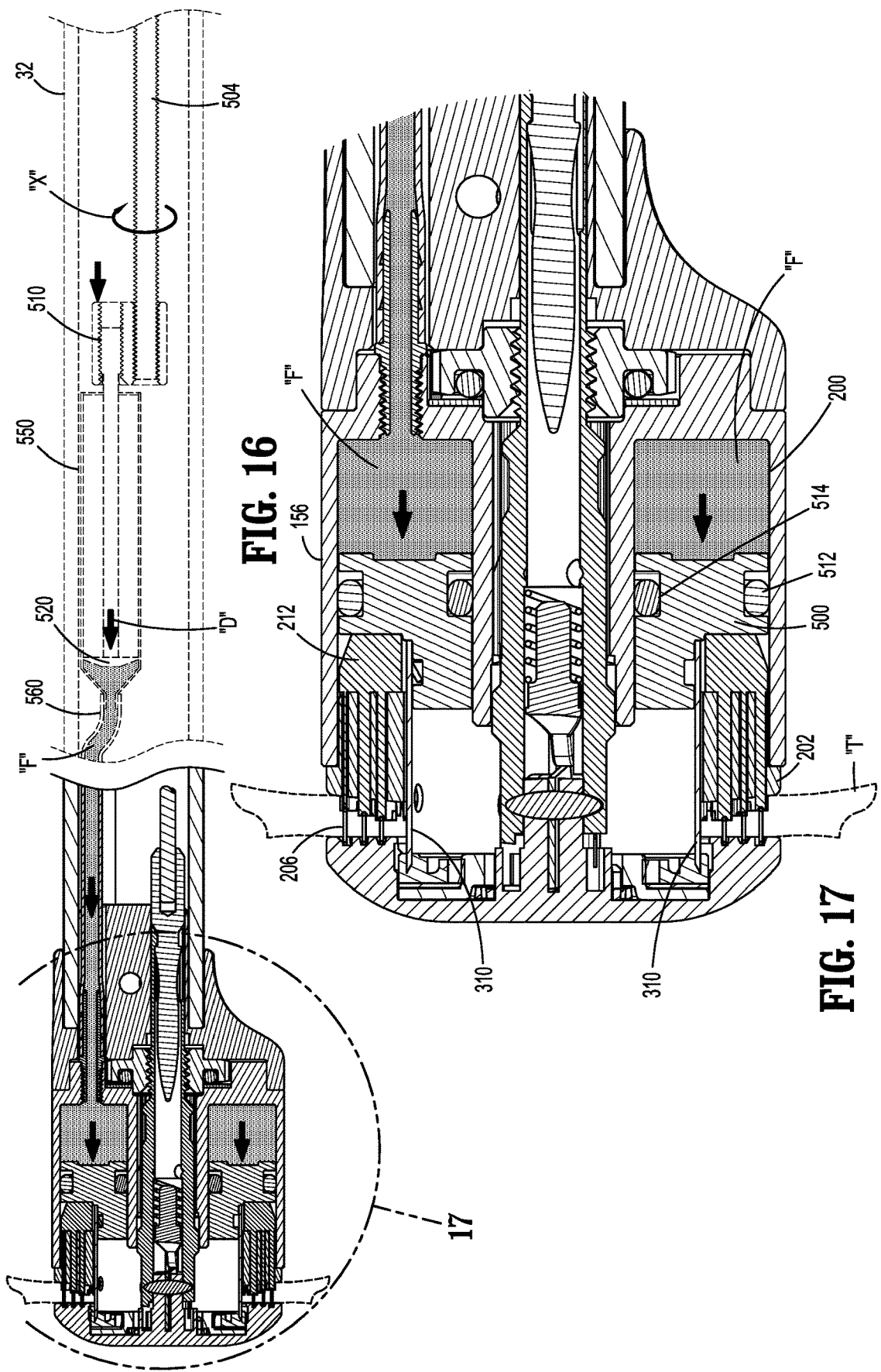

SURGICAL STAPLING DEVICE INCLUDING A HYDRAULIC STAPLE FORMATION MECHANISM

CROSS-REFERENCE TO RELATED APPLICATION

This application claims the benefit of and priority to U.S. Provisional Patent Application Ser. No. 63/149,845, filed on Feb. 16, 2021, the entire disclosure of which is incorporated by reference herein.

BACKGROUND

Technical Field

The disclosure relates to surgical instruments and, more particularly, to an endoscopic stapling device with a flexible shaft that supports an end effector.

Background of Related Art

Surgical stapling devices for performing surgical procedures endoscopically are well known and are commonly used to reduce patient trauma and shorten patient recovery times. Typically, an endoscopic stapling device includes a handle assembly, a rigid elongate body that extends distally from the handle assembly, and an end effector including a tool assembly that is supported on a distal portion of the elongate body. The handle assembly is coupled to the end effector by drive mechanisms that extend through the elongate body and allow a clinician to control operation of the end effector remotely via the handle assembly.

Surgical stapling devices for endoscopic use are available in a variety of configurations including linear and circular. Circular stapling devices are commonly used to perform anastomoses after resections of the large bowel, i.e., colectomies. In a large percentage of colectomy procedures, the portion of the colon that must be resected is in the ascending colon or the transverse colon which cannot be easily accessed by a circular stapling device having a rigid shaft. As such, these procedures are typically performed during an open colectomy procedure which result in increased patient trauma and recovery time.

A continuing need exists in the medical arts for a stapling device having a flexible shaft for accessing a surgical site.

SUMMARY

In accordance with the disclosure, a shell assembly includes a shell housing defining a cavity, a plurality of staples, a staple cartridge supported on the shell housing, a pusher assembly positioned within the cavity of the shell housing, and a hydraulic piston configured to engage the pusher assembly to impart axial displacement to the pusher assembly and form a fluid tight seal against the shell housing. The staple cartridge defines slots that receive the plurality of staples. The pusher assembly includes a plurality of pushers arranged in an annular configuration to eject the plurality of staples from the staple cartridge. Supply of a fluid into the cavity of the shell housing advances the hydraulic piston, which, in turn, advances the pusher assembly to eject the plurality of staples from the staple cartridge.

In an aspect, the shell housing may include an annular guide in the cavity that defines a bore therethrough.

In another aspect, the shell assembly may further include an annular knife supported on the hydraulic piston for concomitant axial displacement therewith.

In yet another aspect, the hydraulic piston may define inner and outer circumferential grooves configured to receive respective inner and outer O-rings.

In still yet another aspect, the inner O-ring may be configured to engage the annular guide of the shell housing.

In still yet another aspect, the shell housing may include a clamp gear rotatably supported therein.

In still yet another aspect, the clamp gear may be aligned with the annular guide of the shell housing.

In an aspect, a proximal portion of the shell housing may include an inner lip defining a cutout to rotatably support a clamp input gear such that the clamp input gear operatively engages the clamp gear.

In another aspect, the inner lip may define a bore in communication with the cavity of the shell housing.

In accordance with another aspect of the disclosure, a surgical stapling device includes an adapter assembly and a tool assembly. The adapter assembly includes a flexible outer tube, a first drive assembly extending through the flexible outer tube, a second drive assembly extending through the flexible outer tube, and a third drive assembly. The first drive assembly includes a flexible approximation link and an anvil retainer secured to the flexible approximation link. The second drive assembly includes a flexible drive shaft and an input gear secured to the flexible drive shaft. The third drive assembly includes a hydraulic cylinder disposed in the flexible outer tube and a first piston movable within the hydraulic cylinder. The tool assembly is secured to a distal portion of the flexible outer tube and includes an anvil assembly and a shell assembly. The shell assembly includes a housing, a plurality of staples, a clamp gear supported within the housing, a staple cartridge, a pusher assembly, and a second piston. The anvil assembly includes an anvil head and an anvil shaft secured to the anvil head. The clamp gear is operatively engaged with the input gear of the second drive assembly. The staple cartridge is supported on the shell assembly. The staple cartridge defines staple receiving slots that receive the plurality of staples. The pusher assembly is positioned within the shell housing and includes a plurality of pushers to eject the plurality of staples from the staple cartridge. The second piston movably engages the shell housing of the shell assembly in a sealing relation and operatively engages the pusher assembly. Activation of the first drive assembly through a first clamping stage retracts the flexible articulation link to move the anvil retainer proximally to move the anvil assembly from an open position to a partially clamped position in which the anvil retainer is operatively engaged with the clamp gear. Activation of the second drive assembly through a second clamping stage moves the anvil retainer farther proximally to move the anvil assembly from the partially clamped position to a fully clamped position. Activation of the third drive assembly advances the first piston to direct the fluid into the housing of the shell assembly to advance the second piston, thereby advancing the pusher assembly.

In an aspect, the anvil shaft may have a threaded outer portion configured to be in registration with the clamp gear when the anvil assembly is in the partially retracted position.

In another aspect, the anvil shaft may be releasably coupled to the anvil retainer.

In yet another aspect, the surgical stapling device may further include a handle assembly. The proximal portion of the adapter assembly may be coupled to the handle assembly.

In still yet another aspect, the adapter assembly may include a flexible fluid supply tube interconnecting the hydraulic cylinder and the housing of the shell assembly.

In accordance with still yet another aspect of the disclosure, a surgical stapling device includes an adapter assembly and a tool assembly. The adapter assembly includes a flexible outer tube, a first drive assembly extending through the flexible outer tube, a second drive assembly extending through the flexible outer tube, and a third drive assembly. The first drive assembly includes a flexible approximation link and an anvil retainer secured to a distal portion of the flexible approximation link. The second drive assembly includes a flexible drive shaft and an input gear secured to a distal portion of the flexible drive shaft. The third drive assembly includes a hydraulic cylinder, a first piston, and a flexible tube in fluid communication with the hydraulic cylinder. The tool assembly is secured to a distal portion of the flexible outer tube and includes an anvil assembly and a shell assembly. The anvil assembly includes an anvil head and an anvil shaft secured to the anvil head. The shell assembly includes a shell housing, a staple cartridge, a pusher assembly, a second piston, and a clamp gear. The shell housing defines a cavity in fluid communication with the flexible tube of the third drive assembly. The staple cartridge is supported on the shell housing and defines staple receiving slots that receive a plurality of staples. The pusher assembly is configured to eject the plurality of staples from the staple cartridge. The pusher assembly is positioned within the cavity of the shell housing and includes a plurality of pushers arranged in an annular configuration. The plurality of pushers is transitionable from a retracted position to an advanced position to eject the plurality of staples from the staple cartridge. The second piston is movable within the cavity and operatively engages the pusher assembly. The clamp gear is rotatably supported within the shell housing of the shell assembly and is engaged with the input gear of the second drive assembly. Activation of the first drive assembly through a first clamping stage retracts the flexible approximation link to move the anvil retainer proximally to move the anvil assembly from an open position to a partially clamped position, in which, the anvil shaft is operatively engaged with the clamp gear. Activation of the second drive assembly through a second clamping stage moves the anvil retainer farther proximally to move the anvil assembly from the partially clamped position to a fully clamped position. Activation of the third drive assembly advances the first piston in the hydraulic cylinder to direct a fluid into the cavity of the shell housing through the flexible tube, thereby advancing the pusher assembly.

BRIEF DESCRIPTION OF THE DRAWINGS

Various aspects of the disclosure are described hereinbelow with reference to the drawings, which are incorporated and constitute a part of this specification, wherein:

FIG. 14 is a side cross-sectional view of the adapter assembly of FIG. 13 taken along section line 13-13;

FIG. 15 is an enlarged view of the indicated area of detail of FIG. 14;

FIG. 16 is a side cross-sectional view of the adapter assembly of FIG. 14, illustrating actuation of a firing mechanism of FIG. 14; and FIG. 17 is an enlarged view of the indicated area of detail of FIG. 16.

DETAILED DESCRIPTION

Figure 1:
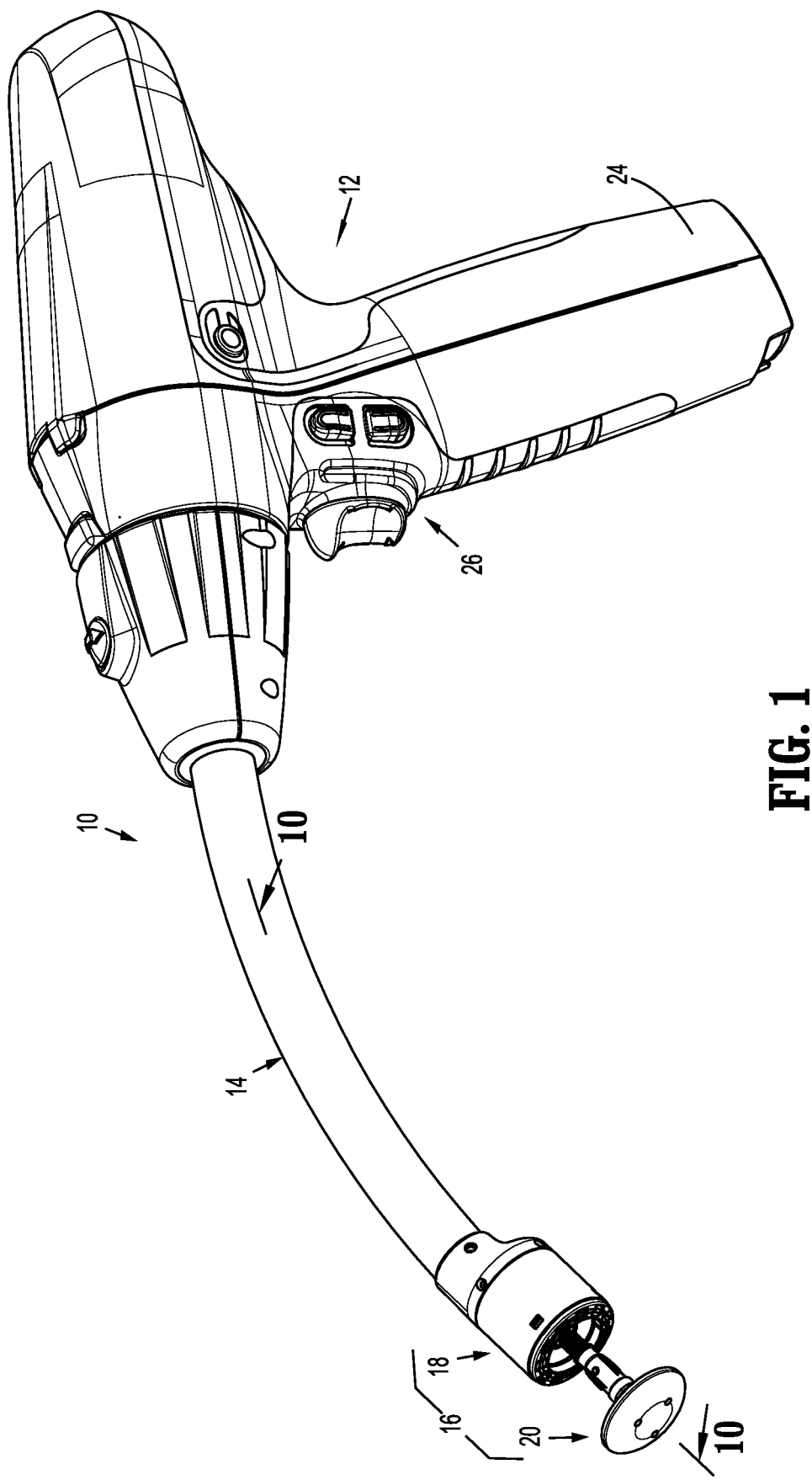
FIG. 1 is a perspective view of a surgical stapling device in accordance with the disclosure.

The disclosed surgical instrument is described in detail with reference to the drawings, in which like reference numerals designate identical or corresponding elements in each of the several views. As used herein, the term "distal," as is conventional, will refer to that portion of the instrument, apparatus, device, or component thereof which is farther from the user, while the term "proximal" will refer to that portion of the instrument, apparatus, device, or component thereof which is closer to the user. As used herein, the terms parallel and perpendicular are understood to include relative configurations that are substantially parallel and substantially perpendicular up to about + or −10 degrees from true parallel and true perpendicular. In the following description, well-known functions or constructions are not described in detail to avoid obscuring the disclosure in unnecessary detail.

With reference to FIG. 1, a surgical instrument in accordance with the disclosure is generally designated as 10 and is in the form of a powered stapling device used to create an anastomosis between two anatomical lumens such as, e.g., colon or esophagus. The surgical instrument 10 provides flexibility to facilitate introduction and positioning of the surgical instrument 10 into a body cavity through natural orifices or incisions around the contours and curvatures of the anatomy within the body cavity, as will be described. The surgical instrument 10 includes a powered handheld electromechanical device, shown generally as a handle assembly 12, an adapter assembly 14, and a tool assembly 16. The tool assembly 16 includes a shell assembly 18 and an anvil assembly 20 that is supported for movement in relation to the shell assembly 18 between an open position (FIG. 1) and a clamped position (FIG. 15). The handle assembly 12 includes a stationary grip 24 that supports actuation buttons 26 for controlling operation of various functions of the surgical instrument 10 including approximation of the shell and anvil assemblies 18, 20, firing of staples 206 (FIG. 3) from the shell assembly 18, and cutting or coring of tissue "T" (FIG. 17).

The surgical instrument 10 is an electrically powered stapling device. As such, the handle assembly 12 may support a motor, control circuitry, and a battery or battery pack (not shown) for driving various mechanisms of the adapter assembly 14 to facilitate approximation of the shell and anvil assemblies 18, 20, firing of staples 206 from the shell assembly 18, and cutting or coring of tissue "T" (FIG. 17). Examples of electrically powered stapling devices including a handle assembly suitable for use with the disclosed surgical instrument 10 can be found in U.S. Pat. No. 9,055,943 (the '943 Patent), U.S. Pat. No. 9,023,014 (the '014 Patent), and U.S. Publication Nos. 2018/0125495, and 2017/0340351.

Figure 2:
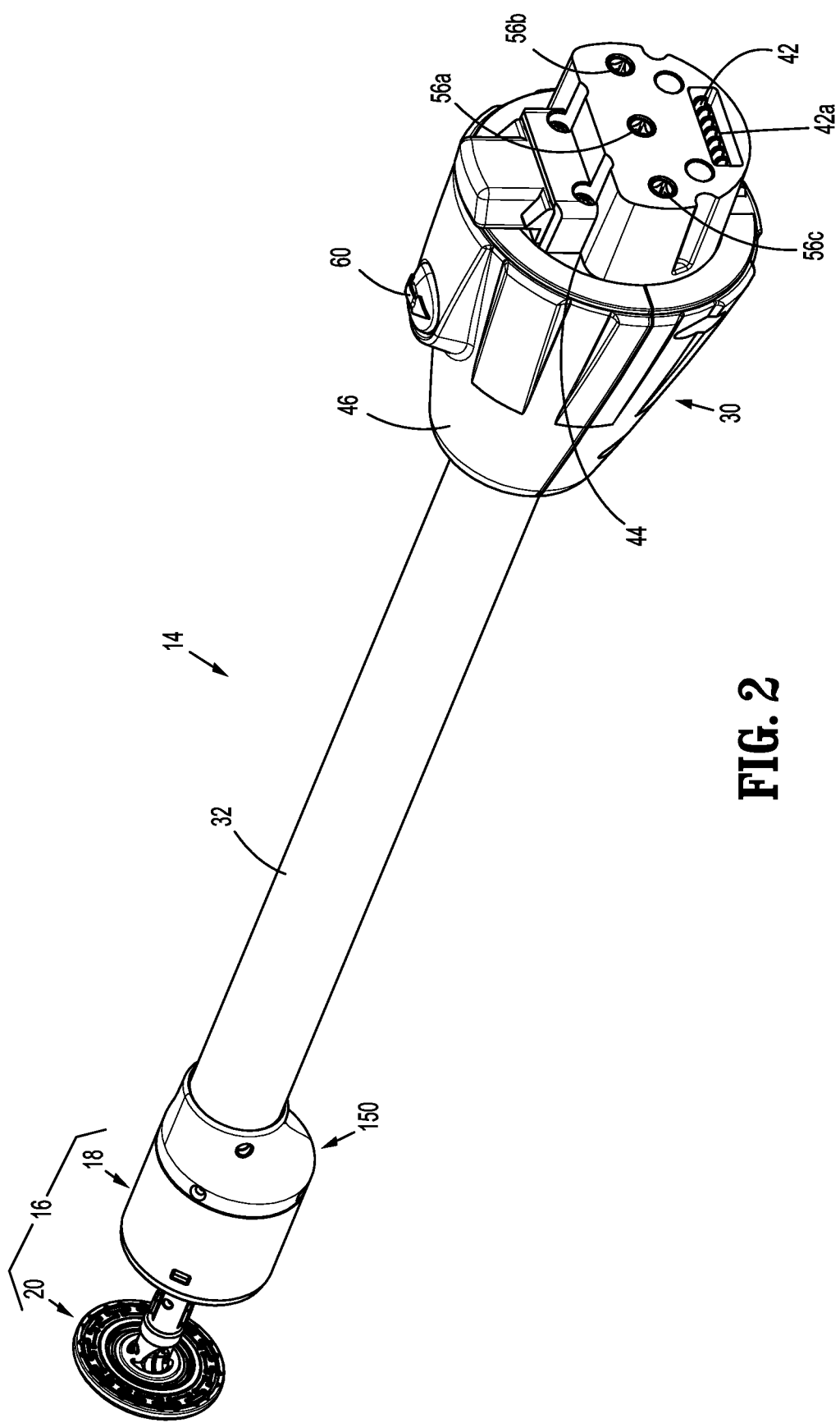
FIG. 2 is a perspective view of an adapter assembly and tool assembly of the surgical stapling device of FIG. 1.
Figure 3:
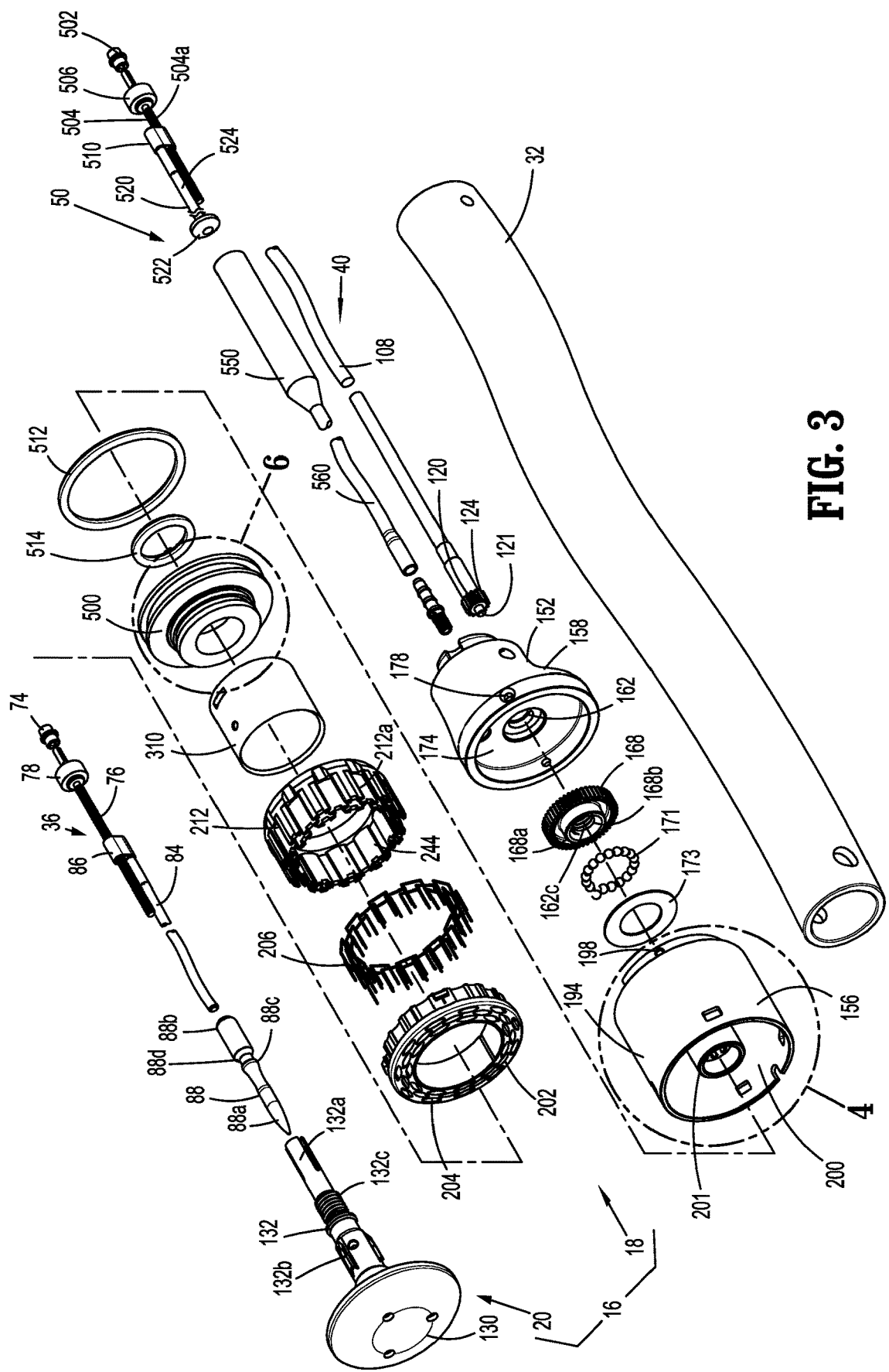
FIG. 3 is an exploded perspective view of the tool assembly of the adapter assembly of FIG. 2 with parts separated.

FIGS. 2 and 3 illustrate the adapter assembly 14 that includes a proximal housing assembly 30, a flexible outer tube 32, a first drive assembly 36, a second drive assembly 40, and a third drive assembly 50. The proximal housing assembly 30 includes a hub 44, a rotation knob 46 that is rotatably supported on the hub 44, and an electrical coupling member 42. The hub 44 defines through bores 56*a*, 56*b*, and 56*c* that receive proximal ends of the first, second, and third drive assemblies 34, 40, 50 of the adapter assembly 14. The electrical coupling member 42 includes proximally extending contacts 42*a* that are positioned to engage contacts in the handle assembly 12 (FIG. 1) when the adapter assembly 14 is coupled to the handle assembly 12 to electrically couple the control circuitry (not shown) in the handle assembly 12 to sensors (not shown) in the adapter assembly 14 and/or tool assembly 16 to facilitate control of the operation of the surgical instrument 10 as known in the art. The hub 44 also supports an adapter release button 60 which can be depressed to facilitate separation of the adapter assembly 14 from the handle assembly 12.

FIG. 3 further illustrates the first drive assembly 36 including a drive connector 74, a threaded drive shaft 76, and a bearing 78. The bearing 78 is received within the through bore 56*a* (FIG. 2) of the hub 44 and defines a through bore that receives an unthreaded proximal end portion of the threaded drive shaft 76 such that the threaded drive shaft 76 is rotatably supported within the bearing 78. The drive connector 74 is fixedly secured to the proximal end of the threaded drive shaft 76 and defines a recess that receives a first drive member (not shown) of the handle assembly 12 (FIG. 1). Under such a configuration, the drive connector 74 imparts rotational input from the handle assembly 12 to the threaded drive shaft 76 within the rotation knob 46 (FIG. 2).

The threaded drive shaft 76 of the first drive assembly 36 is coupled to a flexible approximation link 84 by a threaded coupling member 86. The threaded coupling member 86 defines a threaded bore that receives the threaded drive shaft 76. When the threaded drive shaft 76 is rotated within the rotation knob 46 (FIG. 2) and the flexible outer tube 32 (FIG. 2), the threaded coupling member 86 translates along the threaded drive shaft 76 to cause axial displacement of the flexible approximation link 84 within the flexible outer tube 32 between an advanced position in which the threaded coupling member 86 is positioned on a distal portion of the threaded drive shaft 76 and a retracted position in which the threaded coupling member 86 is positioned on a proximal portion of the threaded drive shaft 76. The distal end of the flexible approximation link 84 is secured to an anvil retainer 88 that includes a distal trocar portion 88*a* and a proximal portion 88*b*. The proximal portion 88*b* of the anvil retainer 88 is coupled to the flexible approximation link 84 such that the anvil retainer 88 is movable with the flexible approximation link 84 between advanced and retracted positions.

Similar to the first drive assembly 36, the second drive assembly 40 includes a drive connector (not shown), a flexible drive shaft 108, and a bearing (not shown). The bearing is received within the through bore 56*b* (FIG. 2) defined in the hub 44 and defines a through bore that receives a proximal end of the flexible drive shaft 108 such that the flexible drive shaft 108 is rotatably supported within the bearing. The drive connector is fixedly secured to the proximal end of the flexible drive shaft 108 and defines a recess that receives a second drive member (not shown) of the handle assembly 12 (FIG. 1). The drive connector is rotatable to impart rotation to the flexible drive shaft 108 within the rotation knob 46 (FIG. 2) and outer tube 32 (FIG. 2). The flexible drive shaft 108 has a distal portion that supports a clamp input gear 120 that includes a cylindrical body portion having a protrusion 121 and a distal gear member 124. The clamp input gear 120 is fixedly secured to the flexible drive shaft 108 such that rotation of the flexible drive shaft 108 imparts concomitant rotation to the clamp input gear 120.

The third drive assembly 50 includes a drive connector 502, a drive shaft 504, a bearing 506, a piston assembly 520, a hydraulic cylinder 550, and a fluid supply tube 560. The bearing 506 is received within the through bore 56*c* (FIG. 2) defined in the hub 44 and defines a through bore that receives an unthreaded proximal end portion of the drive shaft 504 such that the drive shaft 504 is rotatably supported within the bearing 506. The drive connector 502 is fixedly secured to a proximal end of the drive shaft 504 and defines a recess that receives a third drive member (not shown) of the handle assembly 12 (FIG. 1). Under such a configuration, the drive connector 502 imparts concomitant rotation to the drive shaft 504 within the rotation knob 46 (FIG. 2).

The drive shaft 504 has a threaded portion 504*a* that is threadably coupled to a coupling member 510. In particular, the coupling member 510 defines a threaded bore that receives the threaded portion 504*a* of the drive shaft 504. The coupling member 510 is also coupled to the piston assembly 520 for movement as a single construct. The piston assembly 520 includes a piston head 522 and a piston shaft 524 connected to the coupling member 510. Under such a configuration, when the drive shaft 504 is rotated within the rotation knob 46 (FIG. 2) and the flexible outer tube 32 (FIG. 2), the coupling member 510 translates along the drive shaft 504 to cause axial displacement of the piston assembly 520 within the flexible outer tube 32 between an advanced position in which the piston head 522 is positioned at a distal end portion of the hydraulic cylinder 550 and a retracted position in which the piston head 522 is positioned at a proximal end portion of the hydraulic cylinder 550. The piston assembly 520 is received in the hydraulic cylinder 550 to displace a volume of fluid into and out of the hydraulic cylinder 550 during the transition between the advanced and retracted positions of the piston head 522. The fluid supply tube 560 is in communication with the hydraulic cylinder 550 and the shell assembly 18 to supply the fluid to the shell assembly 18 to actuate firing of staples 206 and cutting of tissue "T" (FIG. 17), as will be described below.

FIG. 3 further illustrates the tool assembly 16 of the surgical instrument 10 which includes the shell assembly 18 and the anvil assembly 20. The anvil assembly 20 includes an anvil head 130 and an anvil shaft 132. The anvil shaft 132 has a distal portion that is coupled to the anvil head 130 and a proximal portion that is adapted to be releasably coupled to the anvil retainer 88. In aspects of the disclosure, the proximal portion of the anvil shaft 132 includes resilient fingers 132a that define a longitudinal cavity (not shown) that receives the anvil retainer 88. When the anvil retainer 88 is inserted into the longitudinal cavity of the anvil shaft 132, the resilient fingers 132a of the anvil shaft 132 engage and move along an outwardly diverging surface 88c of the anvil retainer 88 and are deformed outwardly to facilitate passage of the anvil retainer 88 into the longitudinal cavity. When the anvil retainer 88 is received within the longitudinal cavity, the resilient fingers 132a of the anvil shaft 132 return to their nondeformed condition and engage an annular shoulder 88d of the anvil retainer 88 to releasably couple the anvil shaft 132 to the anvil retainer 88. The anvil shaft 132 also supports a plurality of longitudinal splines 132b that are spaced about the periphery of the anvil shaft 132. In some aspects of the disclosure, the anvil head 130 is pivotably coupled to the anvil shaft 132. For a more detailed description of an anvil assembly including a pivotable head assembly, see, e.g., U.S. Pat. No. 6,945,444 ("the '444 Patent").

The shell assembly 18 includes a housing assembly 150 (FIG. 2) that includes a proximal housing 152 and a shell housing 156. The proximal housing 152 includes a body 158 configured to receive the first, second, and third drive assemblies 36, 40, 50. In particular, the proximal housing 152 defines a first through bore 162 centrally located along a longitudinal axis "X" of the shell assembly 18. The first through bore 162 receives the flexible approximation link 84 of the first drive assembly 36. The distal portion of the proximal housing 152 includes an annular extension 172 that defines a cavity 174.

Figure 4:
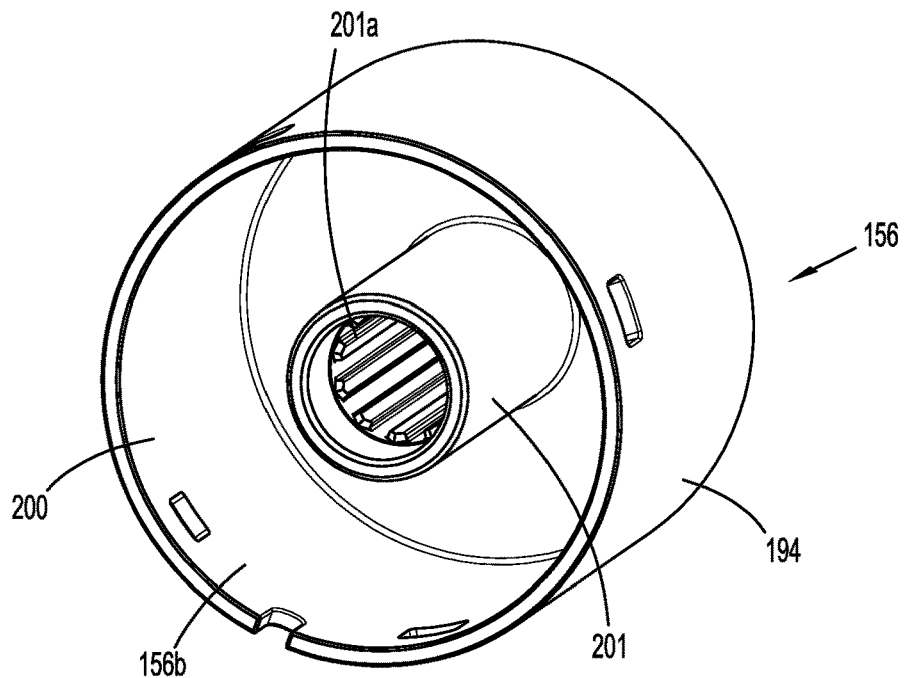
FIG. 4 is an enlarged view of the indicated area of detail of FIG. 3.
Figure 5:
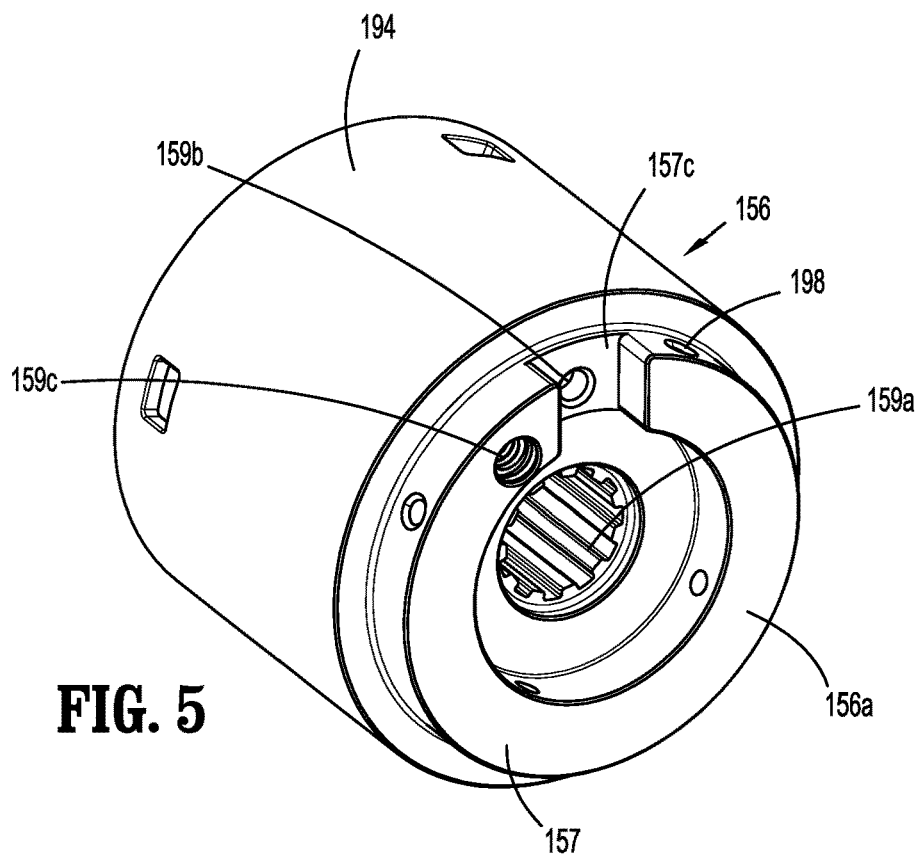
FIG. 5 is a rear perspective view of a shell housing of FIG. 4.

FIGS. 3-5 illustrate the shell housing 156 of the housing assembly 150 including a cylindrical body 194 that has a proximal portion 156a and a distal portion 156b. The proximal portion 156a of the cylindrical body 194 has an inner lip 157 (FIG. 5) that is received in the cavity 174 (FIG. 3), i.e., within the annular rim 172, of the proximal housing 152. In particular, the inner lip 157 defines a cutout 157c.

The proximal portion 156a of the shell housing 156 defines first, second, and third bores 159a, 159b, 159c. With brief reference to FIG. 3, the proximal portion 156a rotatably supports a clamp gear 168 in registration with the first bore 159a. The clamp gear 168 includes a cylindrical extension 168a that is concentrically disposed with respect to the clamp gear 168. The cylindrical extension 168a defines a bore 168b that is in communication with the first through bore 162 of the proximal housing 152 and the first bore 159a of the shell housing 156. The clamp gear 168 supports a thrust bearing 171 and a thrust washer 173 about the cylindrical extension 168a to facilitate rotation of the clamp gear 168. The shell housing 156 and the proximal housing 152 are fixedly secured together using screws (not shown) which are received through openings 198 in the shell housing 156 and openings 178 in the rim 172 of the proximal housing 152.

In this manner, the shell housing 156 extends distally from the proximal housing 152. The shell housing 156 defines an inner cavity 200, in which, the shell housing 156 includes an annular guide 201. The first bore 159a of the shell housing 156 extends through the annular guide 201. The second bore 159b is configured to receive a protrusion 121 of the clamp input gear 120 of the second drive assembly 40 to rotatably support the clamp input gear 120 within the cutout 157c of the shell housing 156. The third bore 159c is in communication with the inner cavity 200 and is connected to the fluid supply tube 560 (FIG. 3) of the third drive assembly 50.

Further, the annular guide 201 has an inner surface including splines 201a to guide the complementary splines 132b of the anvil assembly 20.

The distal portion 156b of the shell housing 156 supports an annular staple cartridge 202 that defines staple receiving slots 204. Each of the staple receiving slots 204 receives a staple 206. In one aspect of the disclosure, the staple receiving slots 204 are formed in one or more circular rows in the annular staple cartridge 202. In addition, a pusher assembly 212 is supported in the inner cavity 200 of the shell housing 156 adjacent the annular staple cartridge 202. The pusher assembly 212 includes a plurality of pushers 212a that is coupled together to form an annular configuration. The shell assembly 18 further includes an annular knife 310 disposed radially inward of the pusher assembly 212. The annular knife 310 and the pusher assembly 212 are operatively coupled to a piston 500 disposed within the inner cavity 200 of the shell housing 156.

Figure 6:
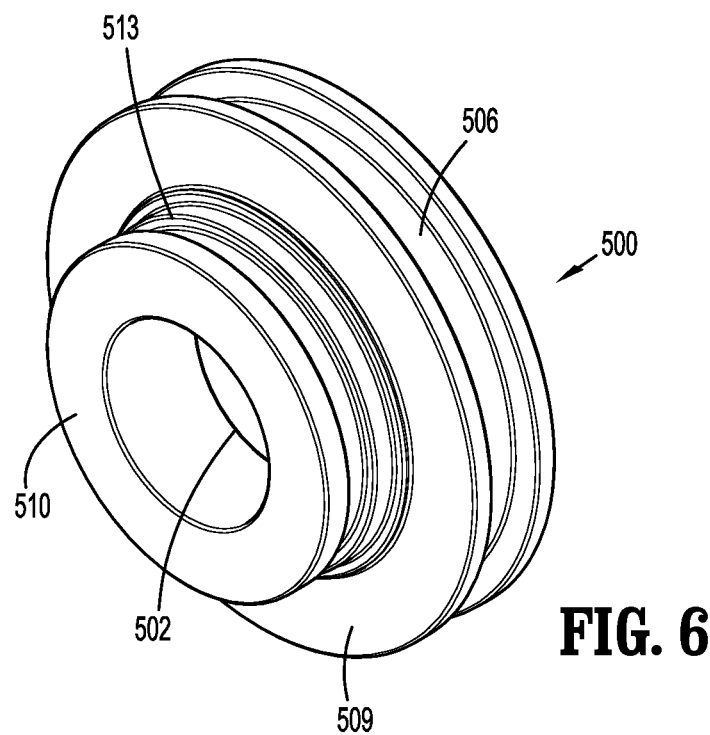
FIG. 6 is an enlarged view of the indicated area of detail of FIG. 3.
Figure 7:
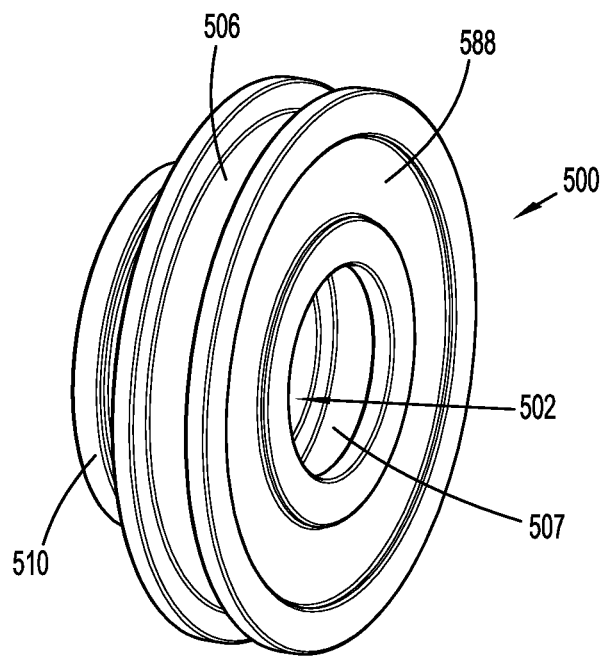
FIG. 7 is a rear perspective view of a piston of FIG. 6.

In particular, FIGS. 6 and 7 illustrate the piston 500 having an annular configuration defining a bore 502 therethrough. The piston 500 further includes an annular extension 510 configured to secure the annular knife 310 thereto. In particular, the annular extension 510 defines a circular groove 513 (FIG. 6) to receive a radial tang (not shown) of the annular knife 310 in order to enhance securement therewith. The piston 500 further includes a flange portion 509 configured to engage the pusher assembly 212 (FIG. 3). The piston 500 defines an outer circumferential groove 506 on an outer surface of the piston 500 and an inner circumferential groove 507 on an inner surface of the piston 500. First and second o-rings 512, 514 are received in the outer and inner circumferential grooves 506, 507, respectively, to thereby form a fluid tight seal against the shell housing 156. The proximal portion of the piston 500 defines a recess 588 to contain the fluid "F" (FIG. 15) therein.

Figure 8:
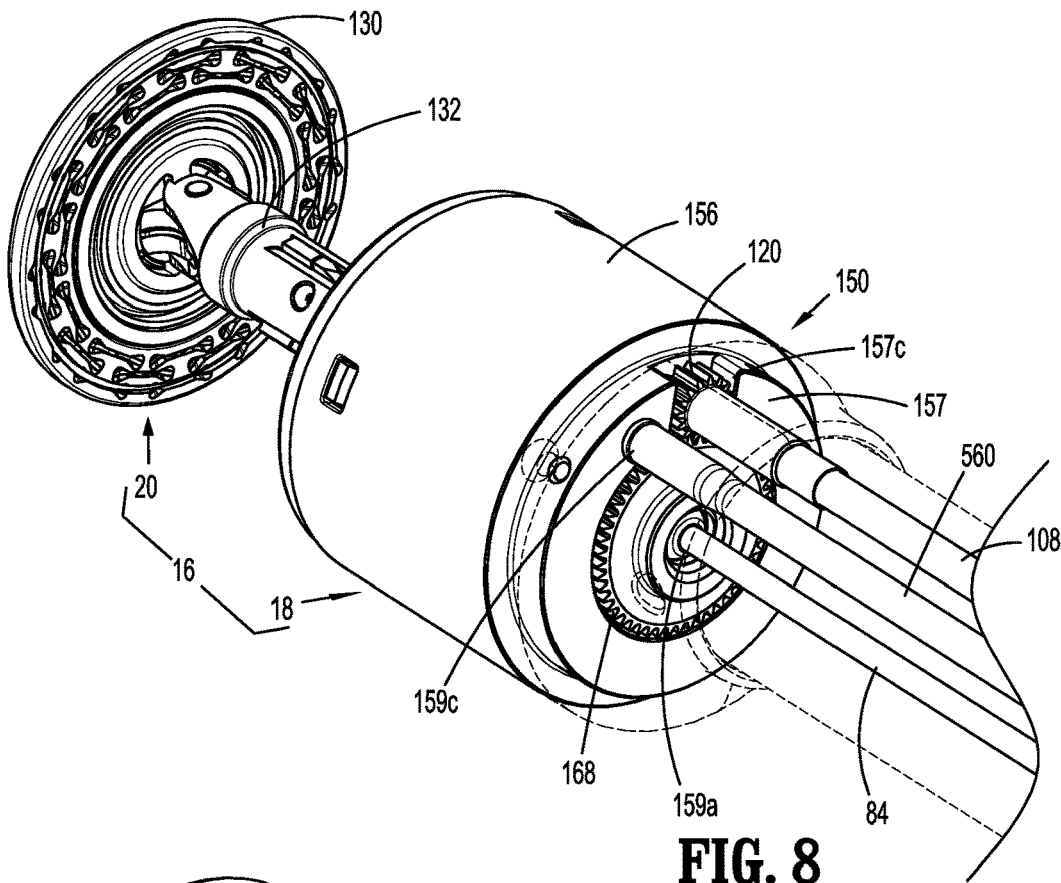
FIG. 8 is a perspective view of the tool assembly of FIG. 2.
Figure 9:
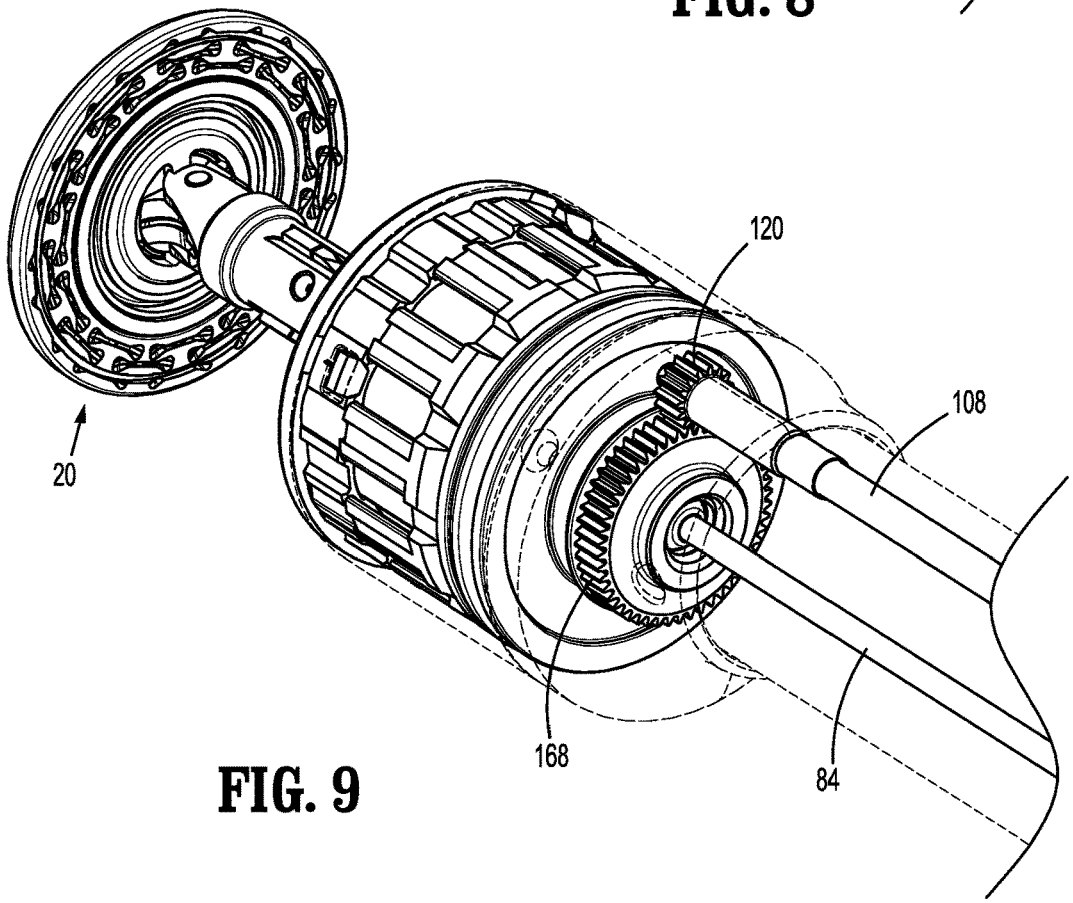
FIG. 9 is a perspective view of the tool assembly of FIG. 8 with the shell housing removed.

FIGS. 8 and 9, illustrate the flexible approximation link 84 of the first drive assembly 36 extending through the first bore 159a of the shell housing 156. The clamp input gear 120 of the second drive assembly 40 is rotatably supported in the cutout 157c of the inner lip 157 of the shell housing 156. The clamp input gear 120 engages the clamp gear 168 to impart rotation to the clamp gear 168. The clamp gear 168 has a threaded inner surface 162c (FIG. 3) that is configured to threadably engage a threaded portion 132c (FIG. 3) of the anvil shaft 132, as will be described below. The fluid supply tube 560 is connected to the third bore 159c of the shell housing 156 to supply a hydraulic fluid to the inner cavity 200 (FIG. 4) of the shell housing 156, thereby enabling axial displacement of the piston 500 to effect firing of staples and cutting of tissue, as will be described below.

Figure 10:
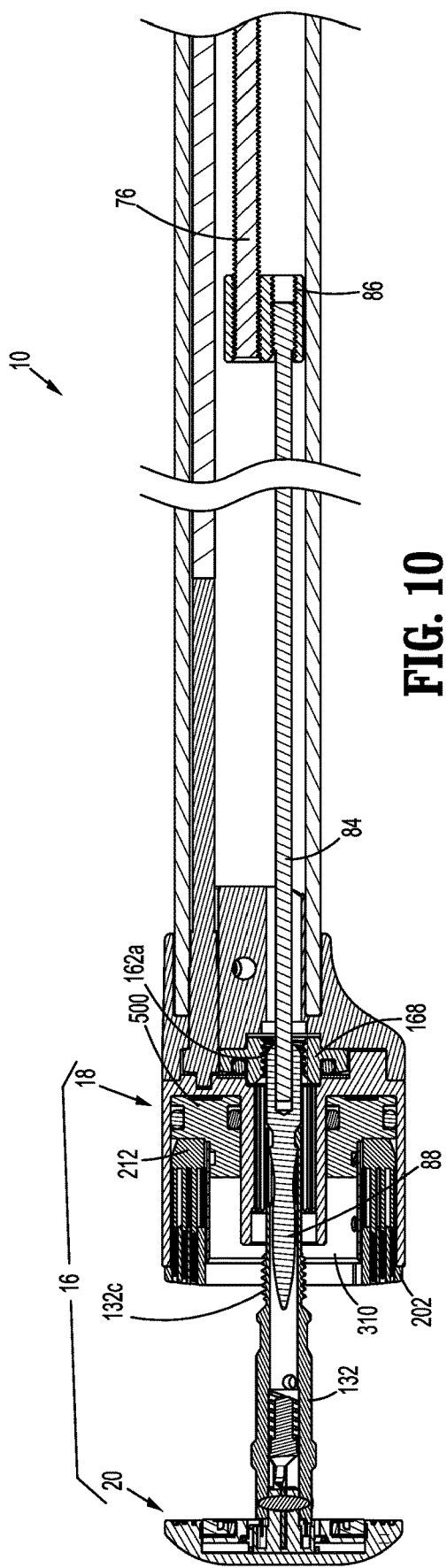
FIG. 10 is a side cross-sectional view taken along section line 10-10 of FIG. 1.
Figure 11:
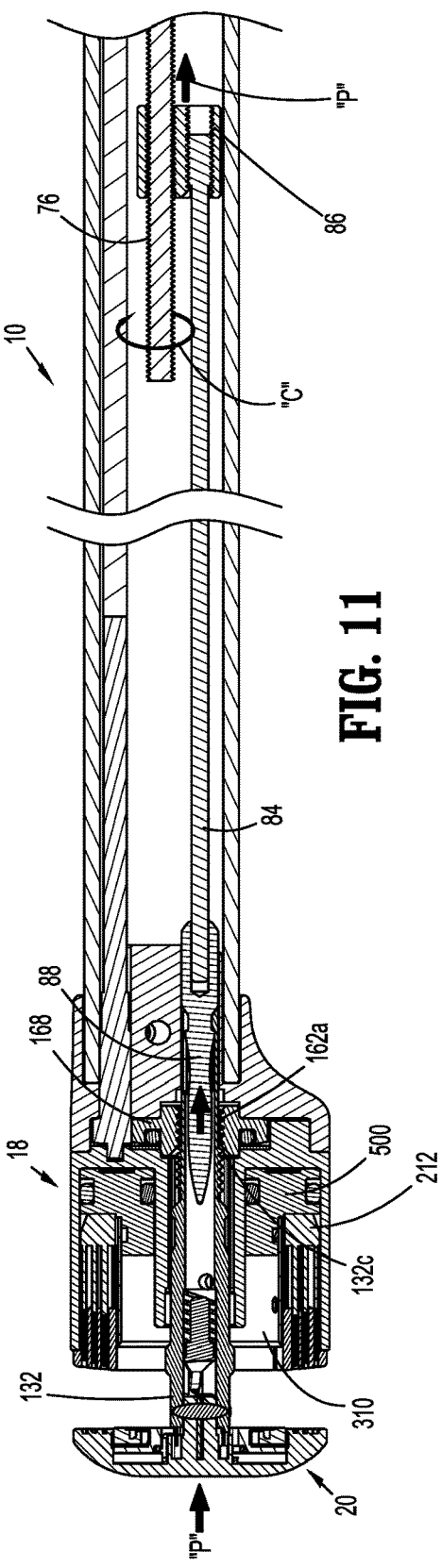
FIG. 11 is a partial side cross-sectional view of the adapter assembly of FIG. 10, illustrating retraction of the anvil assembly.

FIGS. 10 and 11 illustrate retraction of the anvil assembly 20 relative to the shell assembly 18. In particular, FIG. 10 illustrates the surgical instrument 10 in a pre-fired position with the anvil assembly 20 coupled to the anvil retainer 88 and the tool assembly 16 in the open position. In this position, a distal end of the threaded drive shaft 76 of the first drive assembly 36 (FIG. 3) is received in the threaded coupling member 86 and the flexible approximation link 84 of the first drive assembly 36 is in its advanced position such the anvil assembly 20 is spaced from the annular staple cartridge 202 of the shell assembly 18. In addition, the piston 500, the pusher assembly 212, and the annular knife 310 are in their retracted positions within the shell housing 156 of the shell assembly 18.

The drive connector 74 (FIG. 3) of the first drive assembly 36 receives a rotational input from an actuator (not shown) of the handle assembly 12 (FIG. 1). Rotational input provides rotation to the threaded drive shaft 76 in the direction of, e.g., an arrow "C" in FIG. 11, which, in turn, causes axial displacement of the threaded coupling member 86 in the direction of an arrow "P", relative to the threaded drive shaft 76. The anvil retainer 88 is coupled to the threaded coupling member 86 via the flexible approximation link 84. Under such a configuration, the anvil assembly 20 that is coupled to the anvil retainer 88 is transitionable between an advanced position (FIG. 10) and a retracted position (FIG. 11). In particular, when the anvil assembly 20 is in the retracted position, the threaded portion 132c of the anvil shaft 132 is placed in registration with the threaded inner surface 162a of the clamp gear 168.

Figure 12:
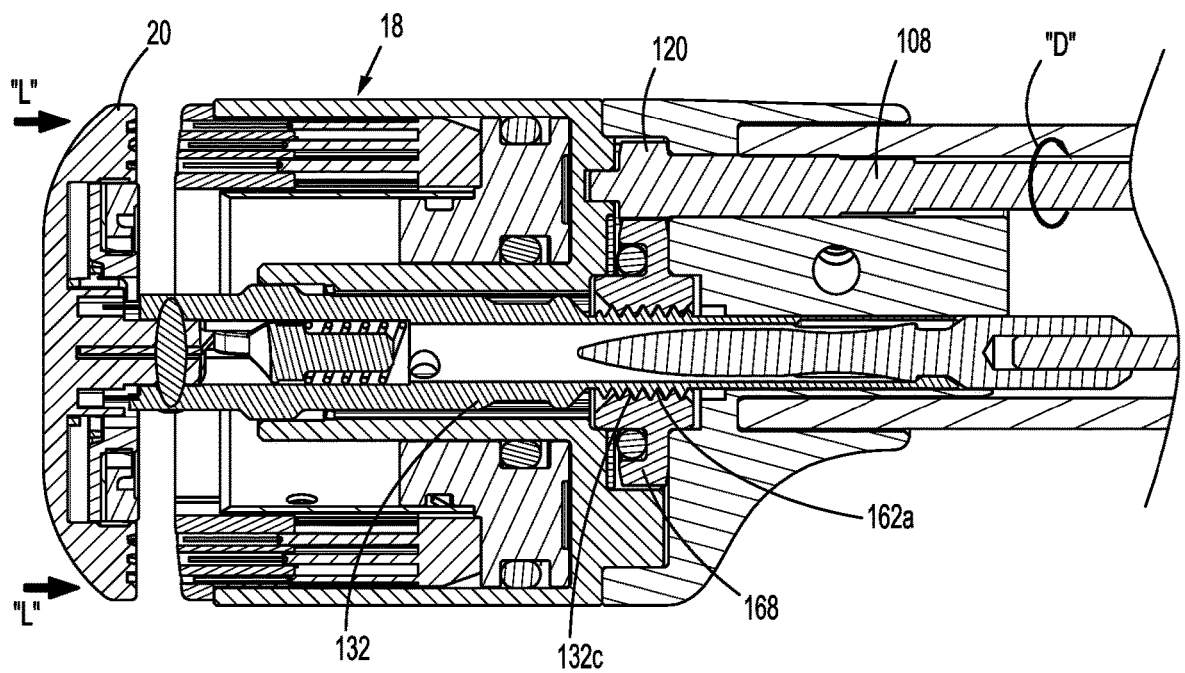
FIG. 12 is a partial side cross-sectional view of the adapter assembly of FIG. 10, illustrating close approximation of an anvil assembly.
Figure 13:
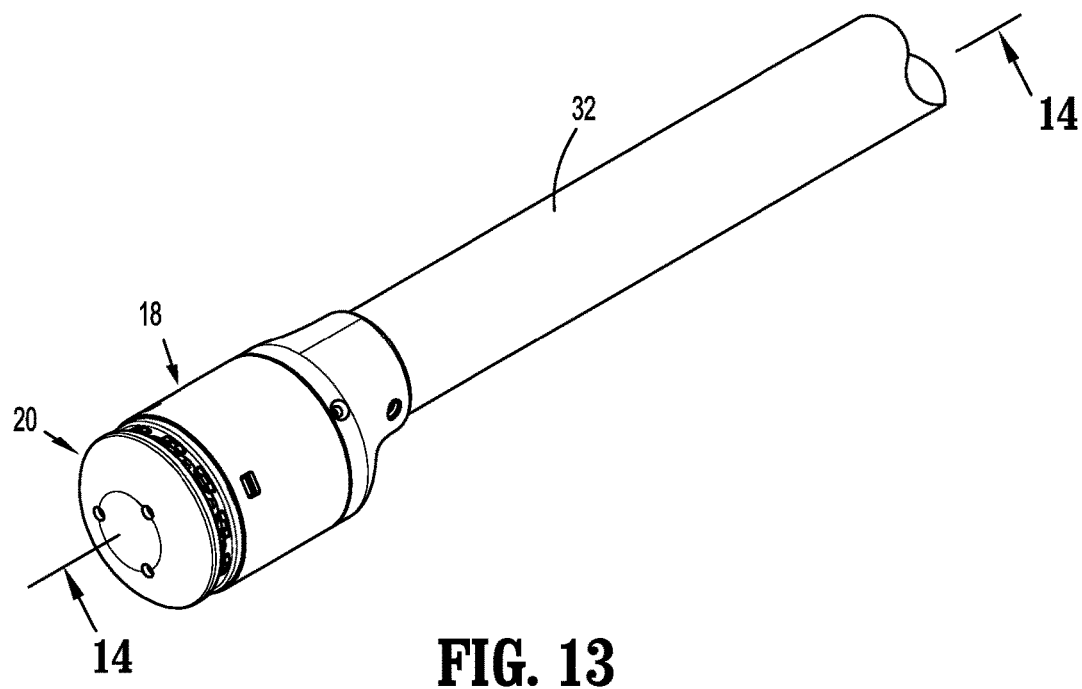
FIG. 13 is a partial perspective view of the adapter assembly of FIG. 2, illustrating close approximation of the anvil assembly.

FIGS. 12 and 13 illustrate close approximation of the anvil assembly 20 relative to the shell assembly 18. Specifically, the surgical instrument 10 is actuated to move the tool assembly 16 through a second clamping stage to a fully clamped position. Close approximation of the anvil assembly 20 is effected when the anvil assembly 20 is in the retracted position through the use of the second drive assembly 40 (FIG. 3). When the anvil assembly 20 is in the retracted position, the threaded portion 132c of the anvil shaft 132 is in registration with the threaded inner surface 162a of the clamp gear 168. Under such a configuration, rotation of the flexible drive shaft 108 imparts concomitant rotation to the clamp input gear 120. The clamp input gear 120 engages the clamp gear 168 to impart rotation thereto. In this manner, rotation of the clamp input gear 120, e.g., in the direction of an arrow "D" (FIG. 12) causes close approximation of the anvil assembly 20 in the direction of arrows "L". Under such a configuration, the clamping forces to move the tool assembly 16 from the partially clamped position to the fully clamped position during the second clamping stage are contained within the housing assembly 150 of the shell assembly 18 and are not distributed through flexible outer tube 32 of the adapter assembly 14.

FIGS. 14-16 illustrate a firing mechanism of the surgical instrument 10. To fire the staples 206 (FIG. 3) from the annular staple cartridge 202, the handle assembly 12 is actuated to activate the third drive assembly 50 (FIG. 3). The drive shaft 504 of the third drive assembly 50 receives rotational input from an actuator of the handle assembly 12. Rotation of the drive shaft 504 causes axial displacement of the coupling member 510, which, in turn, imparts axial displacement to the piston assembly 520. For example, rotation of the drive shaft 504 in the direction of an arrow "X" (FIG. 16) causes axial displacement of the piston assembly 520 in the direction of an arrow "D" which directs the hydraulic fluid "F" in the hydraulic cylinder 550 towards third bore 159c (FIG. 5) of the shell housing 156 via the fluid supply tube 560. As the piston assembly 520 travels distally in the hydraulic cylinder 550, the hydraulic fluid "F" is displaced into the inner cavity 200 of the shell housing 156, thereby advancing the piston 500 in the inner cavity 200.

The piston 500 imparts axial displacement to the pusher assembly 212 and the annular knife 310. The pushers 212a advance through the staple receiving slots 204 of the annular staple cartridge 202 to eject the staples 206 from the annular staple cartridge 202 (FIG. 3). In addition, the annular knife 310 is also advanced to cut tissue "T". Through the use of the hydraulic fluid "F" supplied through the fluid supply tube 560, the need for a rigid or a semi-rigid member for the firing mechanism is eliminated. In this manner, a maximum shaft flexibility of the flexible outer tube 32 is effected, while generating adequate firing forces and minimizing the distal length of the device. The flexible outer tube 32 may provide the maximum flexibility to accommodate the contours and curvatures of the anatomical structures of a patient.

Any of the components described herein may be fabricated from either metals, plastics, resins, composites, or the like taking into consideration strength, durability, wearability, weight, resistance to corrosion, ease of manufacturing, cost of manufacturing, and the like. It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

The invention claimed is:

1. A shell assembly comprising:
a shell housing defining a cavity;
a plurality of staples;
a staple cartridge supported on the shell housing, the staple cartridge defining slots that receive the plurality of staples;
a pusher assembly positioned within the cavity of the shell housing and including a plurality of pushers arranged in an annular configuration to eject the plurality of staples from the staple cartridge; and
a hydraulic piston configured to engage the pusher assembly to impart axial displacement to the pusher assembly, the hydraulic piston having inner and outer circumferential grooves, the inner and outer circumferential grooves receiving respective inner and outer O-rings that are configured to form a fluid tight seal against the shell housing,
wherein supply of a fluid into the cavity of the shell housing advances the hydraulic piston, which, in turn, advances the pusher assembly to eject the plurality of staples from the staple cartridge.

2. The shell assembly according to claim 1, the shell housing includes an annular guide in the cavity, the annular guide defining a bore therethrough.

3. The shell assembly according to claim 2, further comprising an annular knife supported on the hydraulic piston for concomitant axial displacement therewith.

4. The shell assembly according to claim 2, wherein the inner O-ring is configured to engage the annular guide of the shell housing.

5. The shell assembly according to claim 2, wherein the shell housing includes a clamp gear rotatably supported therein.

6. The shell assembly according to claim 5, wherein the clamp gear is aligned with the annular guide of the shell housing.

7. The shell assembly according to claim 6, wherein a proximal portion of the shell housing includes an inner lip defining a cutout to rotatably support a clamp input gear such that the clamp input gear operatively engages the clamp gear.

8. The shell assembly according to claim 7, wherein the inner lip defines a bore in communication with the cavity of the shell housing.

9. A surgical stapling device comprising:
 an adapter assembly including:
  a flexible outer tube;
  a first drive assembly extending through the flexible outer tube, the first drive assembly including a flexible approximation link and an anvil retainer secured to the flexible approximation link;
  a second drive assembly extending through the flexible outer tube, the second drive assembly including a flexible drive shaft and an input gear secured to the flexible drive shaft; and
  a third drive assembly including:
   a hydraulic cylinder disposed in the flexible outer tube; and
   a first piston movable within the hydraulic cylinder; and
 a tool assembly secured to a distal portion of the flexible outer tube, the tool assembly including:
  an anvil assembly including an anvil head and an anvil shaft secured to the anvil head; and
  a shell assembly including:
   a housing;
   a plurality of staples;
   a clamp gear supported within the housing of the shell assembly, the clamp gear operatively engaged with the input gear of the second drive assembly;
   a staple cartridge supported on the shell assembly, the staple cartridge defining staple receiving slots that receive the plurality of staples;
   a pusher assembly positioned within the shell housing and including a plurality of pushers to eject the plurality of staples from the staple cartridge; and
   a second piston movably engaging the shell housing of the shell assembly in a sealing relation, the second piston operatively engaging the pusher assembly,
 wherein activation of the first drive assembly through a first clamping stage retracts the flexible articulation link to move the anvil retainer proximally to move the anvil assembly from an open position to a partially clamped position in which the anvil retainer is operatively engaged with the clamp gear,
 activation of the second drive assembly through a second clamping stage moves the anvil retainer farther proximally to move the anvil assembly from the partially clamped position to a fully clamped position, and
 activation of the third drive assembly advances the first piston to direct the fluid into the housing of the shell assembly to advance the second piston, thereby advancing the pusher assembly.

10. The surgical stapling device according to claim 9, wherein the anvil shaft has a threaded outer portion in registration with the clamp gear when the anvil assembly is in the partially retracted position.

11. The surgical stapling device according to claim 10, wherein the anvil shaft is releasably coupled to the anvil retainer.

12. The surgical stapling device according to claim 9, further including a handle assembly, the adapter assembly having a proximal portion coupled to the handle assembly.

13. The surgical stapling device according to claim 9, wherein the adapter assembly includes a flexible fluid supply tube interconnecting the hydraulic cylinder and the housing of the shell assembly such that the hydraulic cylinder and the housing of the shell assembly are in fluid communication.

14. A surgical stapling device comprising:
 an adapter assembly including:
  a flexible outer tube;
  a first drive assembly extending through the flexible outer tube, the first drive assembly including a flexible approximation link and an anvil retainer secured to a distal portion of the flexible approximation link;
  a second drive assembly extending through the flexible outer tube, the second drive assembly including a flexible drive shaft and an input gear secured to a distal portion of the flexible drive shaft; and
  a third drive assembly including a hydraulic cylinder, a first piston, and a flexible tube in fluid communication with the hydraulic cylinder; and
 a tool assembly secured to a distal portion of the flexible outer tube, the tool assembly including:
  an anvil assembly including an anvil head and an anvil shaft secured to the anvil head; and
  a shell assembly including:
   a shell housing defining a cavity in fluid communication with the flexible tube of the third drive assembly;
   a staple cartridge supported on the shell housing, the staple cartridge defining staple receiving slots that receive a plurality of staples;
   a pusher assembly configured to eject the plurality of staples from the staple cartridge, the pusher assembly positioned within the cavity of the shell housing and including a plurality of pushers arranged in an annular configuration, the plurality of pushers transitionable from a retracted position to an advanced position to eject the plurality of staples from the staple cartridge;
   a second piston movable within the cavity and operatively engaging the pusher assembly; and
   a clamp gear rotatably supported within the shell housing of the shell assembly, the clamp gear engaged with the input gear of the second drive assembly,
 wherein activation of the first drive assembly through a first clamping stage retracts the flexible approximation link to move the anvil retainer proximally to move the anvil assembly from an open position to a partially clamped position, in which, the anvil shaft is operatively engaged with the clamp gear,
 wherein activation of the second drive assembly through a second clamping stage moves the anvil retainer farther proximally to move the anvil assembly from the partially clamped position to a fully clamped position, and
 wherein activation of the third drive assembly advances the first piston in the hydraulic cylinder to direct a fluid into the cavity of the shell housing through the flexible tube, thereby advancing the pusher assembly.

15. The stapling device according to claim 14, wherein the tool assembly further includes an annular knife supported on the second piston.

16. The stapling device according to claim 15, wherein the clamp gear has a threaded bore configured to threadably engage a threaded outer portion of the anvil shaft.

17. The stapling device according to claim 16, wherein the second piston includes first and second O-rings configured to engage the shell housing to form a fluid-tight seal.

18. The stapling device according to claim 17, wherein the shell assembly includes an annular guide centrally disposed in the cavity.

19. The stapling device according to claim 18, further including a handle assembly, a proximal portion of the adapter assembly coupled to the handle assembly.

20. The shell assembly of claim 1, further including an annular knife supported on an annular extension of the hydraulic piston, the annular knife including a radial tang that is configured to engage a groove of the annular extension and secure the annular knife to the hydraulic piston.

* * * * *